US010316346B2

(12) United States Patent
Zhu et al.

(10) Patent No.: US 10,316,346 B2
(45) Date of Patent: Jun. 11, 2019

(54) METHOD AND APPARATUS FOR DISPERSION OF MICROBES IN A LIQUID SUSPENSION

(71) Applicant: TB Healthcare Co., Ltd., Foshan (CN)

(72) Inventors: Guofeng Zhu, Foshan (CN); Baizi Mo, Foshan (CN); Hongbo Zhang, Foshan (CN); Jian Hou, Foshan (CN); Weiguo Zhao, Foshan (CN); Lijun Bi, Foshan (CN); Jiaoyu Deng, Foshan (CN); Shengce Tao, Foshan (CN); Haiying Hang, Foshan (CN); Jiawei Li, Foshan (CN); Xiao Yang, Foshan (CN)

( * ) Notice: Subject to any disclaimer, the term of this patent is extended or adjusted under 35 U.S.C. 154(b) by 0 days.

(21) Appl. No.: 14/866,691

(22) Filed: Sep. 25, 2015

(65) Prior Publication Data

US 2016/0090616 A1 Mar. 31, 2016

(51) Int. Cl.

| | |
|---|---|
| *G01N 15/00* | (2006.01) |
| *G01N 21/00* | (2006.01) |
| *B01L 3/00* | (2006.01) |
| *C12Q 1/04* | (2006.01) |
| *G01N 21/59* | (2006.01) |
| *G01N 21/51* | (2006.01) |

(52) U.S. Cl.
CPC ............... *C12Q 1/04* (2013.01); *G01N 15/00* (2013.01); *G01N 21/51* (2013.01); *G01N 21/59* (2013.01); *G01N 2015/003* (2013.01)

(58) Field of Classification Search
CPC ....... C12M 41/06; C12M 41/30; G01N 21/03; G01N 21/11; G01N 21/82; G01N 21/00
See application file for complete search history.

(56) References Cited

U.S. PATENT DOCUMENTS

| | | | | |
|---|---|---|---|---|
| 3,942,683 A | | 3/1976 | Haas | |
| 5,139,745 A | * | 8/1992 | Barr ....................... | G01N 21/76 250/361 C |
| 5,446,544 A | | 8/1995 | Beers | |
| 6,119,510 A | | 9/2000 | Carasso et al. | |
| 6,739,521 B2 | | 5/2004 | Bandemer et al. | |
| 7,430,043 B1 | | 9/2008 | Evans | |
| 7,554,658 B2 | | 6/2009 | Marsteller et al. | |
| 7,808,642 B2 | | 10/2010 | Connelly et al. | |
| 2010/0113983 A1 | | 5/2010 | Heckerman et al. | |
| 2011/0091933 A1 | | 4/2011 | Kanehara | |
| 2012/0312973 A1 | | 12/2012 | D'Costa et al. | |
| 2014/0272938 A1 | | 9/2014 | Loo et al. | |

FOREIGN PATENT DOCUMENTS

| | | |
|---|---|---|
| CN | 102407423 B | 12/2013 |
| EP | 0978557 A2 | 2/2000 |
| WO | WO 2014/150290 A1 | 9/2014 |

OTHER PUBLICATIONS

International Search Report in International Patent Application No. PCT/US2015/052503, dated Dec. 15, 2015, in 2 pages.

* cited by examiner

*Primary Examiner* — Nathan A Bowers
(74) *Attorney, Agent, or Firm* — Duane Morris LLP

(57) ABSTRACT

An apparatus for dispersing microbes in a biological sample such as a liquid suspension sample and measuring turbidity of the liquid suspension is disclosed. The apparatus is configured for dispersing the microbes in a liquid suspension without destroying the integrity of the microbes and measure the turbidity of the sample suspension at the same time or in the same sample set up without having to move the microbe sample from one equipment to another.

14 Claims, 12 Drawing Sheets

1/10            1/10-1/4            1/4

| Fold-Dilution after sample dispersion | Colony number | Colony growth after dispersion | Dispersion method |
|---|---|---|---|
| $10^5$ | >100 |  | Dispersion by grinding |
| $10^5$ | >100 |  | Ultrasound dispersion |
| $10^6$ | 28 |  | Dispersion by grinding |
| $10^6$ | 37 |  | Ultrasound dispersion |

METHOD AND APPARATUS FOR DISPERSION OF MICROBES IN A LIQUID SUSPENSION

CROSS-REFERENCE TO RELATED APPLICATIONS

This application claims priority under 35 U.S.C. § 119 to Chinese Provisional Applications No. 201410503351.4, filed on Sep. 28, 2014, the entire contents of which are incorporated herein by reference.

FIELD OF THE INVENTION

The present invention relates generally to a method and apparatus for dispersing microbes in a liquid suspension sample.

BACKGROUND

During the processing of biological samples, microorganisms, such as *Mycobacterium tuberculosis*, often cluster and therefore need to be dispersed before sample preparation. Existing conventional dispersion methods can involve mechanical grinding, agitation using a bacteria flask, or pipette blending, etc. Mechanical grinding is generally performed manually and the resulting dispersion is poor, non-uniform, and time consuming. The process of grinding and dilution is carried out in an open container, introducing undesirable opportunities for contact with the skin and/or respiratory systems and exposing the laboratory or hospital personnel to potential hidden danger of infection if the sample is an infectious or toxic microorganism.

After being dispersed, microbial suspensions samples can be analyzed. Some tests, such as turbidity tests, have strict requirements concerning the transparency of the vessel holding the sample. In traditional dispersion methods, sample grinding process generates liquid residue that gets dispersed on the vessel walls, and thus can interfere with the vessel's transparency.

Therefore, an improved way of dispersing microbial samples in liquid suspension is desired.

SUMMARY

According to an embodiment, an apparatus for dispersing microbes in a liquid suspension sample and measuring turbidity of the liquid suspension is disclosed. The apparatus comprises: a transparent container for holding a quantity of the liquid suspension in a sealed chamber, the container having a closed bottom end and an open top end, wherein the open top end is closable with a cap; an ultrasonic transducer having a transducer head portion that generates ultrasonic vibrations; a container-receiving guide block for holding the container in an operating configuration in which the container's bottom end and the transducer head are in direct contact, wherein the container-receiving guide block has a top end and a bottom end and a sidewall defining a longitudinally oriented bore extending from the top end to the bottom end of the container-receiving guide block for receiving the container, wherein the bottom end aligns the closed bottom end of the container with the transducer head, and wherein the container-receiving guide block provides a light source for measuring the turbidity of the liquid suspension; a lid assembly, movable between an open position and a closed position, that is configured and adapted for engaging the top end of the container and urge the container toward the transducer head when the container is being held by the container-receiving guide block and the lid assembly is in the closed position, so that the container bottom surface is in contact with the transducer head and the ultrasonic vibrations generated by the transducer head is transmitted through the container wall to the liquid suspension and disperse the microbes in the liquid suspension; a photo diode for measuring the suspension's turbidity; and an opening provided on the sidewall of the container-receiving guide block, the opening providing a viewing access to the container for the photo diode for measuring the liquid suspension's turbidity.

According to another embodiment, the apparatus for dispersing microbes in a liquid suspension sample and measuring turbidity of the liquid suspension comprises: an ultrasonic transducer having a transducer head portion that generates ultrasonic vibrations; a container-receiving guide block for holding a container of microbes in a liquid suspension in an operating configuration in which the container's bottom end and the transducer head come in direct contact, wherein the container-receiving guide block has a top end and a bottom end and a sidewall defining a longitudinally oriented bore extending from the top end to the bottom end of the container-receiving guide block for receiving the container, wherein the bottom end aligns the closed bottom end of the container with the transducer head, and wherein the container-receiving guide block provides a light source for measuring the turbidity of the liquid suspension; a lid assembly, movable between an open position and a closed position, that is configured and adapted for engaging the container and urge the container toward the transducer head when the container is being held by the container-receiving guide block and the lid assembly is in the closed position, so that the container bottom surface is in direct contact with the transducer head and the ultrasonic vibrations generated by the transducer head is transmitted through the container's wall to the liquid suspension and disperse the microbes in the liquid suspension; a photo diode for measuring the suspension's turbidity; and an opening provided on the sidewall of the container-receiving guide block, the opening providing a viewing access to the container for the photo diode for measuring the liquid suspension's turbidity.

According to another aspect of the present disclosure, a method for dispersing microbes in a liquid suspension and measuring the liquid's turbidity is also disclosed. The method comprising:
 (a) providing the liquid suspension sample in a container, wherein the container has a sidewall, closed bottom end, and a closeable top end;
 (b) placing the container in direct contact with an ultrasonic transducer, wherein the ultrasonic energy generated by the transducer passes to the microbes via the sidewall of the container, thereby dispersing the microbes in the liquid suspension sample; and
 (c) measuring the turbidity of the dispersed liquid suspension in the sample. In some embodiments, the step (c) is conducted while the ultrasonic transducer is dispersing the liquid suspension.

The method and apparatus for dispersing microbes in a liquid suspension described herein generally does not disperse liquid droplets to the container wall and thus avoids interference in measuring the turbidity from such surface liquid residue.

BRIEF DESCRIPTION OF THE DRAWINGS

FIG. 6A represents 1/10, FIG. 6B represents 1/10 to 1/4, and FIG. 6C represents 1/4. Prior to detection, the instrument is calibrated using McFarland standard solutions. The turbidity of one exemplary McFarland standard unit is 3×108 CFU/mL. This example illustrates accurate synchronization between McFarland turbidity measurements and automatic dilution volume calculations.

FIG. 11A shows ultrasound disperation using a press cap lid, and FIG. 11B shows ultrasound dispersion using a screw-top lid. Thus, these results show that using exemplary BACspreader apparatus greatly reduces user exposure the bacterial aerosols.

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
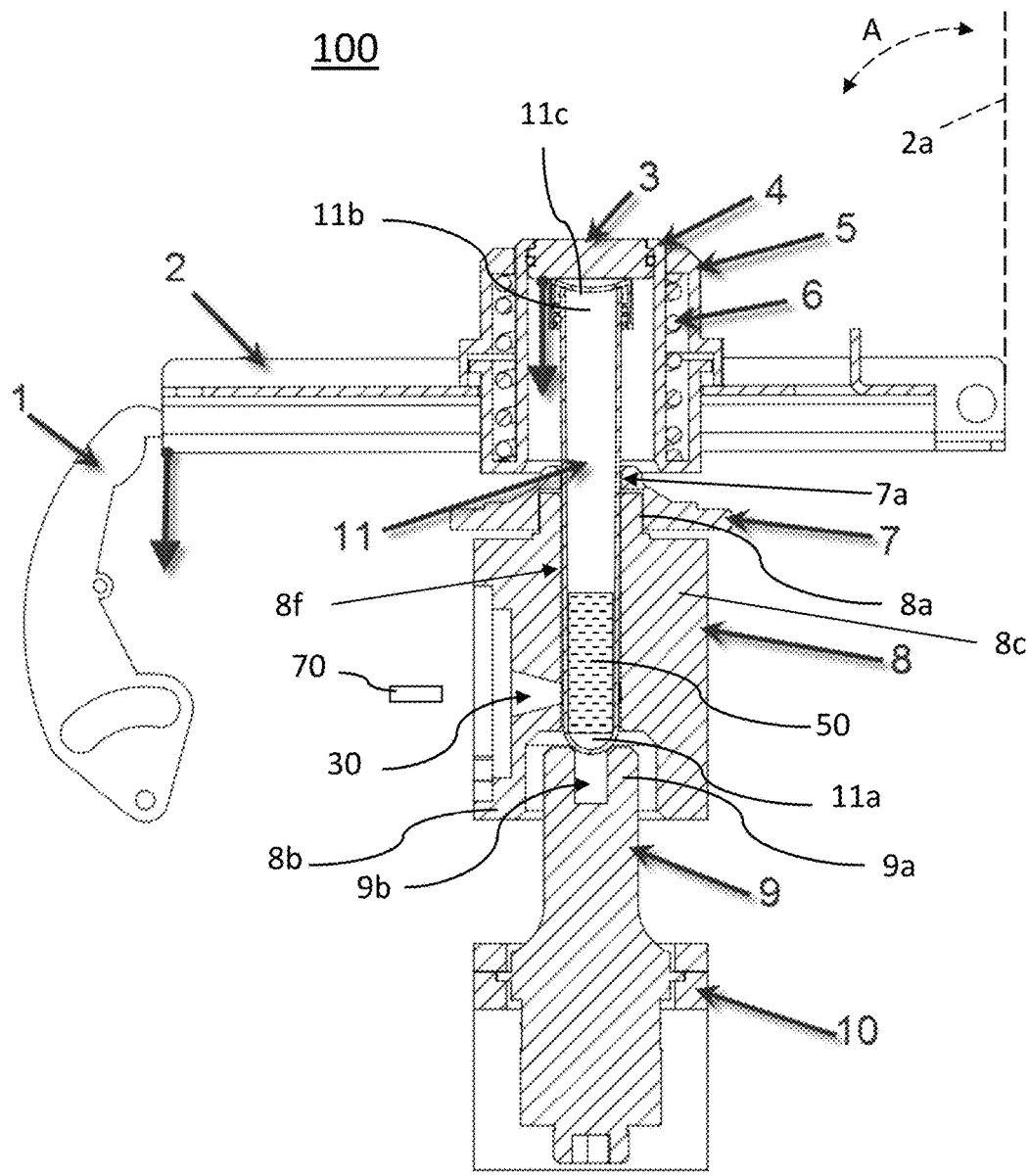
FIG. 1 is a cross-sectional view of the apparatus according to the present disclosure.

In the following detailed description of the preferred embodiments, reference is made to the accompanying drawings which form a part hereof, and in which are shown by way of illustration of specific embodiments in which the invention may be practiced. It is to be understood that other embodiments may be utilized and structural changes may be made without departing from the scope of the present invention.

To address the shortcomings of the conventional microbial dispersion method, the invention disclosed herein provides an improved microbial dispersion method which utilizes ultrasonic energy. The method provides a process that is highly efficient, biologically safe, and easy to use. Ultrasonic energy is transmitted through a transducer to the walls of the container holding the liquid suspension of microbes and serve to disperse microbes. The ultrasonic waves pass directly from the wall into the liquid suspension where they serve to disperse the microbes. The ultrasonic waves achieve the effect of dispersing microbe clumps by ultrasonic cavitation (see Figures). This dispersion process occurs in a sealed container and prevents the dispersion of fluid on the container walls that could affect subsequent operations. The ultrasonic waves are dispersed uniformly through the walls and the bottom of the vessel.

Compared to the conventional dispersion methods, the microbial dispersion methods disclosed herein are greatly improved. The ultrasonic waves are dispersed more uniformly to the walls and the bottom of the container and its surrounding area via the ultrasonic transducer.

In certain general aspects, the exemplary dispersion/detection apparatus of the present disclosure (e.g. BACspreader) can solves the unmet need of dispersing infectious microbes which tend to cluster, thus eliminating the need for traditional manual grinding of microbial colonies. The apparatus and methods disclosed herein are particularly suitable for the preparation of bacteria such as *M. tuberculosis* for drug sensitivity and other tests; thus providing an integrated solution for microbe dispersion and turbidity measurements. In certain embodiments, the exemplary apparatus can combine microbial dispersion functionality with real-time accurate McFarland turbidity measurements. In certain embodiments, the exemplary apparatus described herein can provide automatic dilution volume calculations. In certain embodiments, the exemplary apparatus described herein can perform dispersion and detection/assaying within a closed system, thus greatly reducing user's exposure to biohazards.

In certain aspects, the exemplary apparatus described herein can have instrument characteristics that includes:
1) operating frequency of about 20~40 kHz, power of about 5~200 W;
2) ability to operate for long periods of time, thus, providing a platform to meet flexible diagnostic/laboratory requirements;
3) adaptably configured to work with replacement tubes: 75 mm<L<110 mm, 10 mm<Φ<13 mm;
4) ability to automatically perform closing and locking with a single key opening;
5) has emergency unlocking device; and
6) has working interface that is user-friendly and easy to operate.

In certain other aspects. The exemplary apparatus has the following working characteristics:
1) well designed to integrate microbe dispersion and turbidity measurements;
2) can perform function within the same closed system, thus greatly reducing user exposure to biohazards; and
Ability to synchronizes accurate McFarland turbidity measurements and automatic dilution volume calculations.

Exemplary microorganisms that can be dispersed using the method and apparatus disclosed herein include *Mycobacterium tuberculosis, Staphylococcus aureus, Pseudomonas aeruginosa, Bacillus subtilis, Streptococcus albus* and *Aspergillus niger*. In certain embodiments, any infectious, bacterial/microbial samples with tendency for aggregation can be dispersed using the methods and apparatus of the present disclosure.

When the microbe to be dispersed is *Mycobacterium tuberculosis*, the suitable frequency of the ultrasonic transducer ranges from about 20 KHz to about 80 KHz, the power from about 5 W to about 200 W, and the duration for applying the ultrasonic energy can range from about 15 sec~120 sec or more. *Mycobacterium tuberculosis* can be effectively dispersed using these conditions, and dispersion has no effect on bacterial viability and/or activity.

The present invention also describes a microbial dispersion instrument. The ultrasound dispersion instrument includes an ultrasonic wave generator and an ultrasonic wave transducer, and an electrical connection between the ultrasonic generator and ultrasonic transducer. The described dispersion device can also include a container which serves in microbe dispersion. The bottom end of the container is in close contact with the face of the ultrasonic transducer. The container can be of different sizes, is easily replaced, and the size of the area of close contact between the container and the transducer can be adjusted according to the desired dispersion effect.

The bottom of the vessel is in close contact with the ultrasonic transducer. The hollow in the face of the ultrasonic transducer is compatible with the bottom of the vessel. The close contact between the bottom of the container and the face of the ultrasonic wave transducer improves the dispersion of ultrasonic waves in the area surrounding the bottom of the container.

Referring to FIG. 1, an apparatus 100 for dispersing microbes in a liquid suspension and measuring the turbidity of the liquid suspension is disclosed. The apparatus 100 comprises a transparent vessel/container 11 for holding a quantity of the liquid suspension 50 in a sealed chamber formed by the walls of the container 11. The container 11 has a closed bottom end 11a and an open top end 11b. The open top end is closable with a cap 11c. The open end 11b and the cap 11c are preferably provided with screw threads so that the the cap 11c can be closed tightly to prevent the liquid suspension of microbes from spilling out during the operation of the apparatus. The apparatus is equipped with an ultrasonic transducer 9 that generates ultrasonic vibrations. The transducer 9 has a transducer head portion 9a that is configured and adapted for directly contacting and engaging the bottom end 11a of the container 11.

Figure 2A:
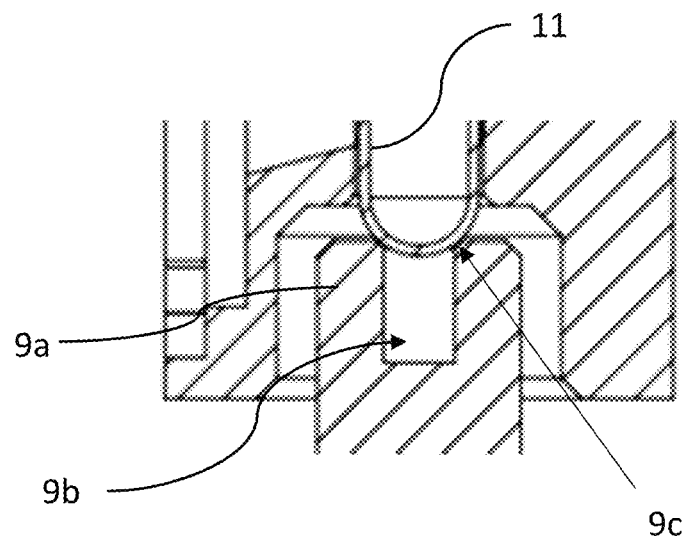
FIG. 2A is a detailed cross-sectional view of the transducer head region of the apparatus including the bottom end of the container 11 showing the direct contact between the transducer head 9a and the bottom end surface of the container holding the liquid suspension of microbes.
Figure 2B:
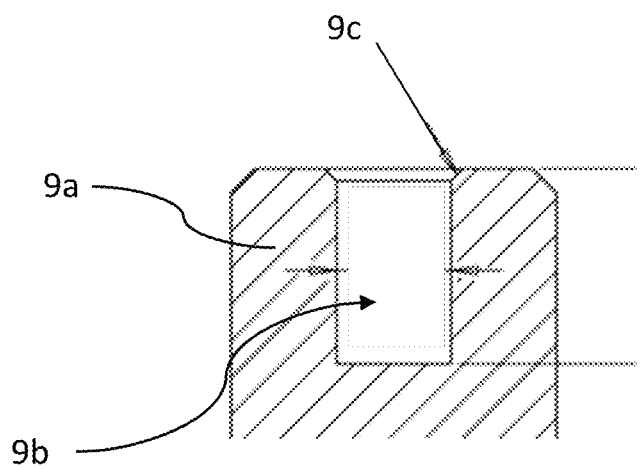
FIG. 2B is another detailed cross-sectional view of the transducer head 9a showing the recess 9b and its structure.
Figure 3:
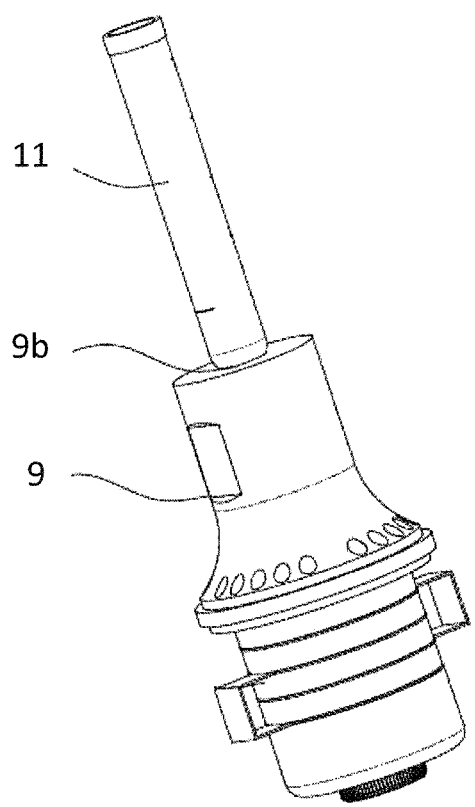
FIG. 3 is a perspective view of the transducer showing the physical arrangement of the container and the transducer in their operational configuration in the apparatus of the present disclosure.
Figure 4:
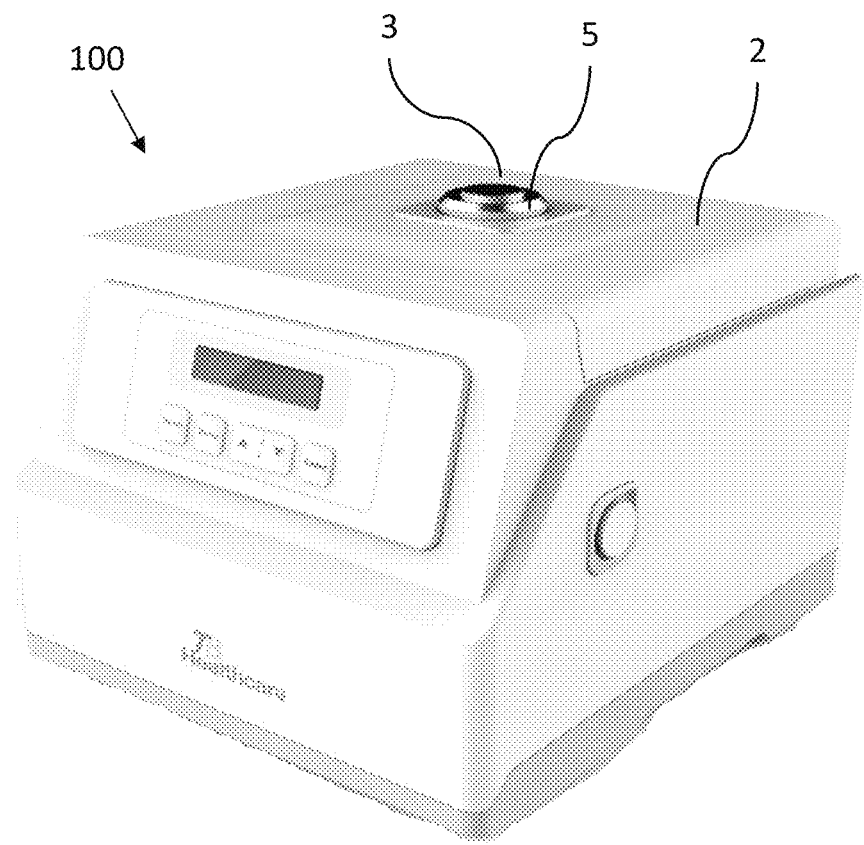
FIG. 4 is an illustrative embodiment of the apparatus embodiment described herein (e.g. BACspreader/microbe dispersion couunter).
Figure 5:
FIG. 5 is an illustrative embodiment of exemplary ultrasonic waves creating a 'cavitation' effect in the liquid, dispersing aggregates into their constituent particles.
Figure 6A:
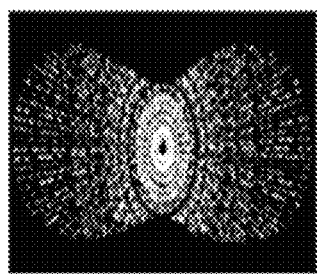
FIGS. 6A, 6B, and 6C is graphic representation of the light scattering-detection configuration that allows accurate measurements of turbidity obtained using a 90° light scattering constant source of illumination. Under proper light intensities, the turbidity of the solution and the 90° scattered light intensity are positively correlated.
Figure 6B:
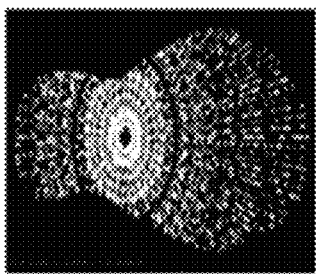
Figure 6C:
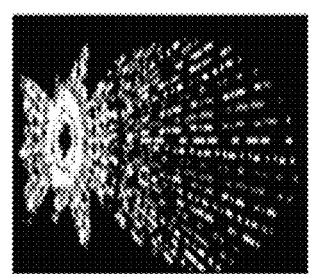
Figure 7A:
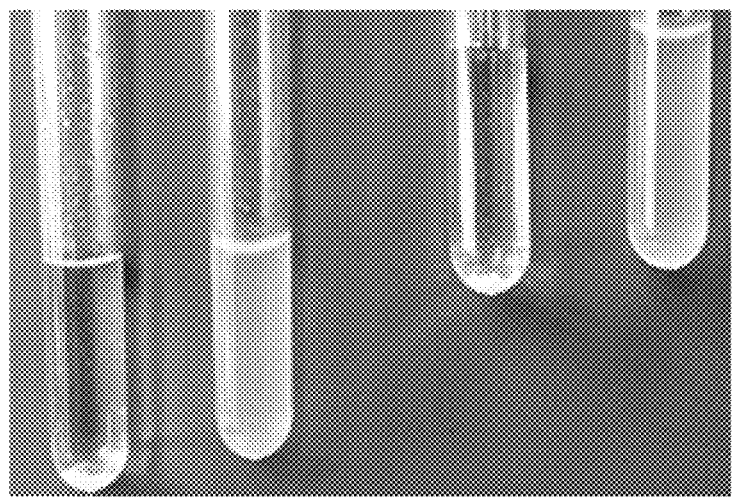
FIGS. 7A and 7B show the efficacy of an exemplary ultrasonic dispersion apparatus embodiment of the present invention (before and after). 10 µl inoculum of (*M. smegmatis*) and 2 ml saline are innoculated per tube (8 ml and 5 ml shown in FIG. 7A). Microbes settle at the bottom of the tube before ultrasound dispersion. After 30 s ultrasound dispersion, the microbes are uniformly dispersed (close up FIG. 7B).
Figure 7B:
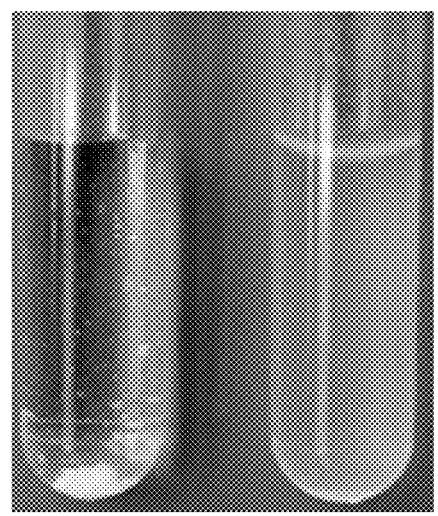
Figure 8A:
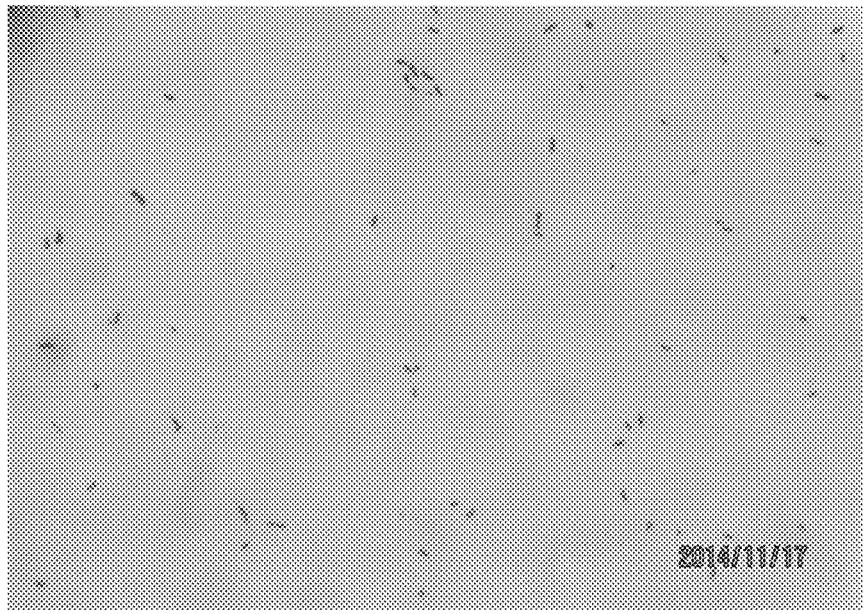
FIGS. 8A and 8B showed the comparison of dispersion using the exemplary BACspreader apparatus vs. traditional manual grinding. *Mycobacterium smegmatis* samples, dispersed either by using the BACspreader (FIG. 8A) or by traditional grinding (FIG. 8B), were diluted to the same McFarland turbidity value. The same volume of sample was then compared by microscopy. Results show that ultrasonic dispersion (FIG. 8A) gives more complete and uniform dispersion than manual grinding (FIG. 8B).
Figure 8B:
Figure 9:
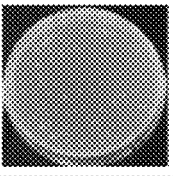
FIG. 9 shows a comparison of dispersion using the exemplary BACspreader apparatus and traditional manual grinding. *Mycobacterium smegmatis* samples were dispersed using BACspreader or by traditional grinding, diluted to the same McFarland turbidity value, then plated and incubated. Colony counts were compared. Results indicated that the BACspreader does not adversely affect the integrity and viability/activity of the microbes in the sample.
Figure 9:
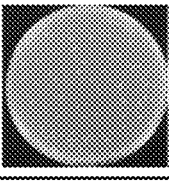
Figure 9:
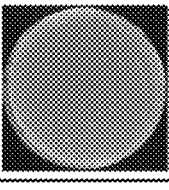
Figure 9:
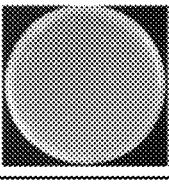
Figure 10:
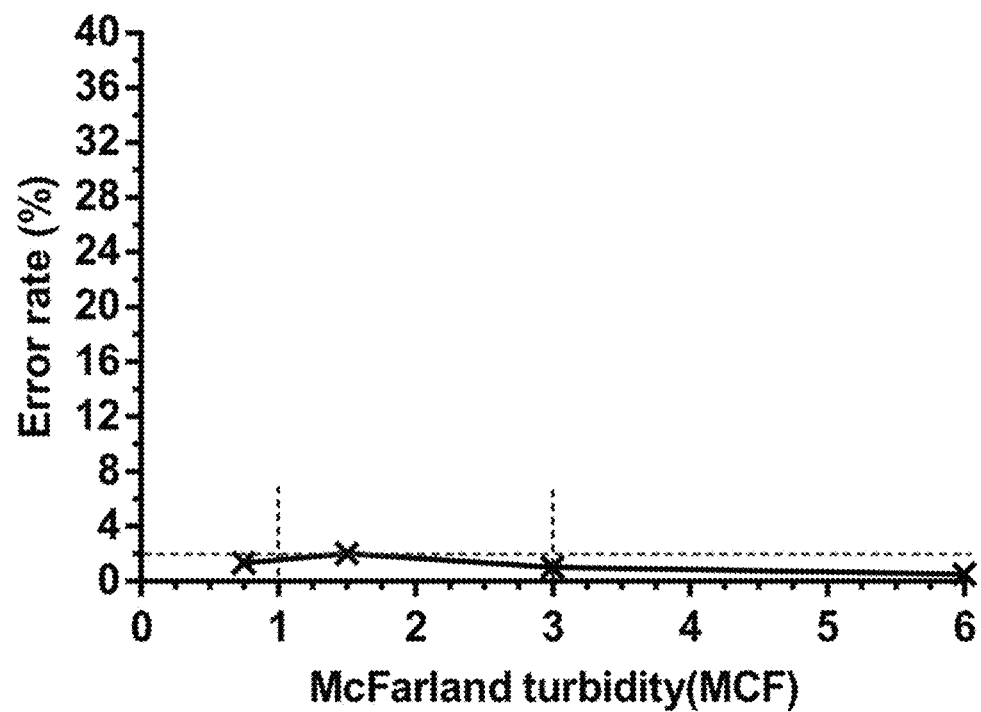
FIG. 10 shows the demonstration of the accuracy of turbidity measurements. After calibrating the instrument using McFarland standard solutions 0 and 6, the turbidity of six McFarland standard solutions (0, 0.5, 0.75, 1.5, 3.0, and 6.0) was determined. Turbidity measurements were recorded and the relationship between the recorded value and the true value was analyzed. Results indicate that the exemplary BACspreader apparatus measures turbidity accurately with an error rate of <2%.
Figure 11A:
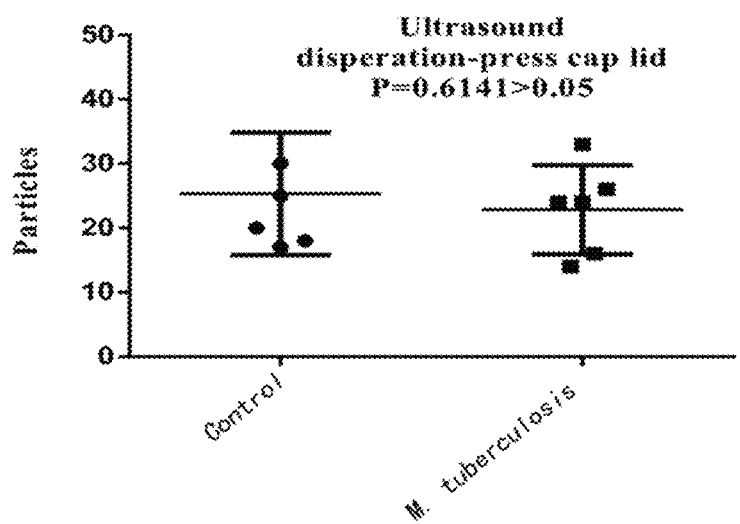
FIGS. 11A and 11B are safety data demonstrating that there is no significant difference between the aerosol generated while dispersing *M. tuberculosis* and the levels of aerosol generated from a blank control.
Figure 11B:
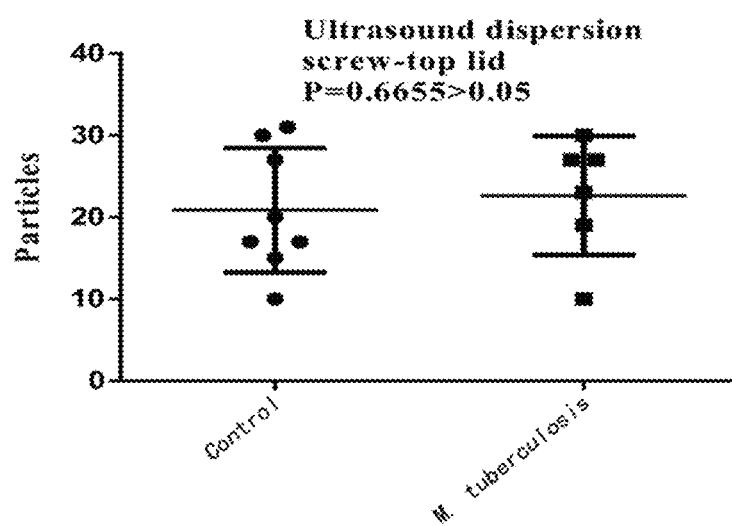
Figure 12:
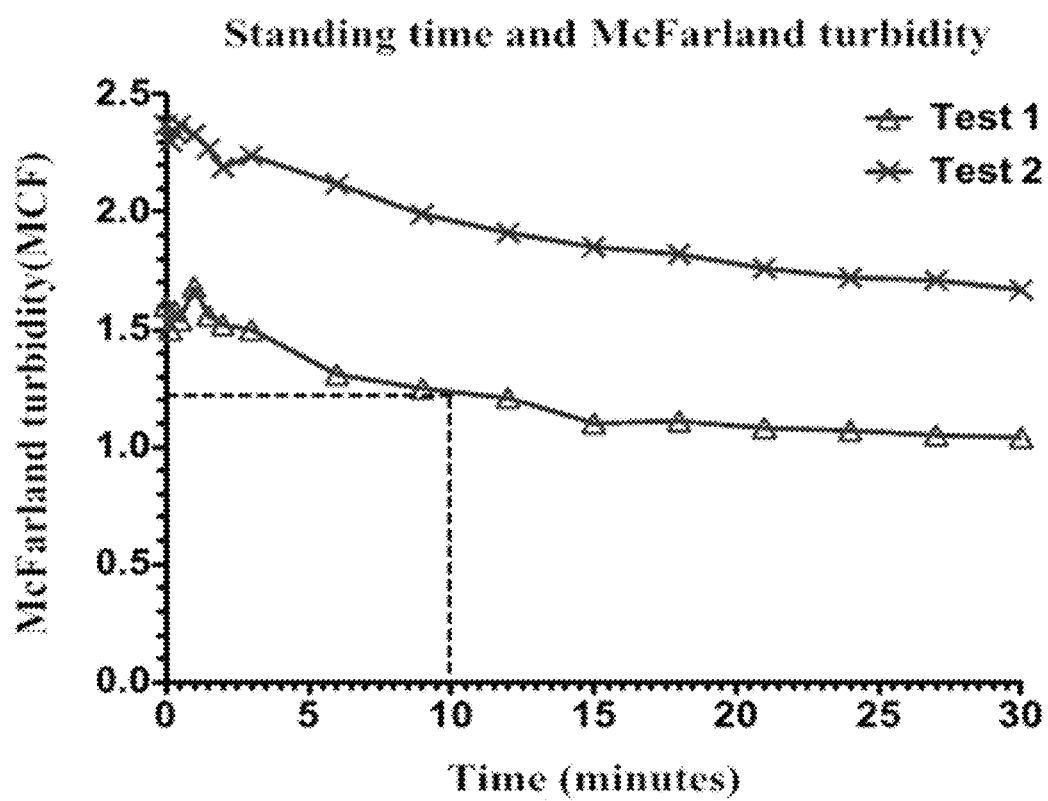
FIG. 12 shows the relationship between standing time and McFarland turbidity value. After dispersion, as standing time increases, bacteria settle and McFarland turbidity measurements gradually decrease. However, exemplary BACspreader apparatus of the present invention can give instant measurements of the turbidity of bacterial suspensions and can thus provide objective measurements that reflect true bacterial concentrations.

Referring to FIGS. 2A and 2B, in a preferred embodiment, the transducer head 9a is provided with a recess (i.e., a blind hole) 9b having a chamfered edge 9c around the annular edge of the recess. The recess 9b allows the transducer head 9a to receive the bottom end 11a of the container which generally has a curved contour as shown. The chamfered edge 9c of the recess 9b also allows more intimate direct contact between the transducer head 9a and the container's bottom end 11a for efficient transfer of ultrasonic vibration from the transducer head to the container 11. The chamfered edge 9c has a width of 0.75 mm and a chamfer angle of 45°.

The ultrasonic transducer 9 in the dispersion instrument described operates at a frequency in the range of about 20 KHz to about 80 KHz, a power range of about 5 W to about 200 W. Microbial dispersion under these conditions is effective, and does not influence the activity of the sample.

By changing the mode of action of ultrasonic waves, the ultrasonic waves pass through the transducer and are dispersed evenly via the walls of the container to disperse the microbe, with no need for a liquid medium between the transducer and the container, thus realizing the purpose of dispersion. The instrument is efficient and convenient, and is easy to operate.

The apparatus 100 also includes a container-receiving guide block 8 for holding the container 11 in an operating configuration. In the operating configuration, the container is in an upright orientation as shown and the container's bottom end 11a and the transducer head 9a are in direct contact. The container-receiving guide block 8 has a top end 8a and a bottom end 8b and a sidewall 8c defining a longitudinally oriented bore 8f extending from the top end 8a to the bottom end 8b of the container-receiving guide block for receiving the container 11. The bottom end 8b aligns the closed bottom end 11a of the container with the transducer head 9a to enable dispersion of the microbes in the liquid suspension 50 by ultrasonic energy.

The apparatus 100 also includes a lid assembly 2, movable between an open position and a closed position. The position of the lid assembly 2 shown in FIG. 1 is the closed position and the open position is represented by the dotted outline 2a. The arrow A shows the hinged open and closing motion of the lid assembly 2. The lid assembly 2 is configured and adapted for engaging the top end 11b of the container and urge the container toward the transducer head 9a when the container 11 is inserted in the container-receiving guide block 8 and the lid assembly is in the closed position as shown. The urging by the lid assembly ensures that the container's bottom surface is in direct contact with the transducer head 9a and the ultrasonic vibrations generated by the transducer head is transmitted through the container wall to the liquid suspension 50 and disperse the microbes in the liquid suspension as desired.

Turbidity of a liquid suspension is measured by considering the propensity of particles suspended in the liquid to scatter a light beam shining on them. To measure turbidity this way requires a light source and a detector set up to the side of the light beam, i.e. 90° to the light beam. The more particles there are in the liquid, more of the source light will be scattered by the particles and reach the detector positioned 90° to the light beam. These measurements can be quantified to certain standardized units well known in the art.

In the apparatus 100 of the present disclosure, the container-receiving guide block 8 is provided with a light source 7 for measuring the turbidity of the liquid suspension 50 in the container 11. The light source 7 is provided near the top end 8a of the container-receiving guide block so that the light shines downward into the liquid suspension 50. The light source 7 is provided with a hole 7a, which is aligned with the longitudinally oriented bore 8f of the container-receiving guide block 8, for receiving the container 11 therethrough. A photo diode 70 is provided for detecting the light scattered by the microbes in the liquid suspension 50 so that the suspension's turbidity can be measured. An opening or a window 30 is provided on the sidewall 8c of the container-receiving guide block 8 to accommodate the photo diode 70 so that the photo diode 70 can detect the scattered light coming from the liquid suspension 50.

In one embodiment, the apparatus can be configured with an appropriate controller or programmed with an appropriate controlling processor so that the dispersion of the microbes in the liquid suspension by the ultrasonic energy and the turbidity measurement of thus properly dispersed liquid suspension can be conducted in serial sequence or simultaneously. The two modes may be selected depending on the particular microbes that are being sampled so that more optimal processing sequence can be chosen.

Referring to FIGS. 2A and 2B, in some embodiments, the container 11 has a cylindrical shape and the recess 9b provided in the transducer head 9a has a circular opening having a chamfered edge 9c. The recess 9b allows the transducer head 9a to accommodate the various shapes that may be presented by the bottom end 11a of the container 11. The chamfered edge 9c makes the contact with the container along the annular edge of the recess 9b for providing a close contact between the container bottom surface and the transducer head for efficient transfer of ultrasonic vibration from the transducer head to the container. In the illustrated example, the bottom end 11a has a spherical contour.

In some embodiments, the lid assembly 2 is provided with a spring-loaded mechanism for engaging the top end 11b of the container and urge the container 11 toward the transducer head 9a. The spring-loaded mechanism comprises a receptacle 4 for receiving the top end 11b of the container including the screw cap 11c. The receptacle 4 is nested inside a hub 5. As can be seen in FIG. 1, the hub 5 is provided with an opening through which the receptacle 4 fits in slidable (in longitudinal direction) manner. Thus, the receptacle 4 is situated within the hub 5 and can slide up and down. The structures of the receptacle 4 and the hub 5 are configured to form a chamber 5a between the sidewalls of the receptacle 4 and the hub 5 and a coil spring 6 is captured inside the chamber 5a. The configuration is such that the coil spring 6 is under compression and urges against the receptacle 4 and the hub 5. The coil spring 6 pushes the hub 5 upward and it pushes the receptacle 4 downward in the orientation of FIG. 1. The hub 5 is affixed to the lid assembly 2 so that when the lid assembly 2 is in closed position and the latch 1 locks the lid assembly 2 into a stationary position, the hub 5 is not movable. However, the receptacle 4 will be movable up and down against the resistance of the coil spring 6. Thus, when the lid assembly 2 is in the closed position as shown and the container 11 is in place, the spring-loaded receptacle 4 will provide a downward force on the top end 11b of the container and urge the container toward the transducer head 9a.

According to another aspect of the present disclosure, the following apparatus 100 for dispersing microbes in a liquid suspension and measuring turbidity of the liquid suspension described above can be manufactured and provided to the end users without the containers for the liquid suspension of microbes. The containers can be supplied to the end users separate from the apparatus 100. The containers can be formed in a variety of sizes and shapes as long as the closed bottom end of the container is appropriately shaped to make the proper direct contact with the recess 9b of the transducer head 9a.

The ultrasonic transducer 9 is driven by an appropriate ultrasonic signal generator which provides high-frequency driving current to the ultrasonic transducer 9. The high-frequency driving current drives the ultrasonic transducer to generate high-frequency, ultrasonic vibrations which is transmitted quickly through the walls of the container 11 and to the liquid suspension inside. The ultrasonic energy creates ultrasonic waves in the liquid suspension which cause cavitation in the liquid, dispersing any clusters of microbes into their constituent microbial particles.

The electronics and control circuits that are used to drive and control the active components of the apparatus 100, such as the ultrasonic transducer 9, the light source 7, and the photo diode 70 are well known in the art. Therefore one of ordinary skill in the art would know how to power these components to make them operational.

When the microorganism is *Mycobacterium tuberculosis*, the optimal frequency of the ultrasonic transducer is about 20 KHz to about 80 KHz, the power is about 5 W to about 200 W, and the reaction time is about 15 s~120 s. The present method does not destroy the viability and/or integrity of the microbes.

The shape of the ultrasound transducer used has no special restrictions, and can be selected to match the shape of the containers used. The frequency and power of the transducer can also be varied depending on the type and weight of the sample. For example, when the sample is *Mycobacterium tuberculosis*, the frequency of the ultrasonic transducer is about 20 KHz-about 80 KHz, and the preferred power is about 5 W-200 W.

In addition, there is a fixture for fixing the vessel in the ultrasound dispersion instrument to ensure that the vessel is in close contact with the face of the ultrasound transducer.

The various embodiments disclosed herein represent examples that fall within the scope of the invention but does not necessarily define the full scope of the invention. The full scope of the invention is defined by the claims provided herein.

What is claimed is:

1. An apparatus for dispersing microbes in a biological sample and measuring turbidity of the biological sample, the apparatus comprising:
   a transparent container for holding a quantity of the biological sample in a sealed chamber, the container having a closed bottom end and an open top end, wherein the open top end is closable with a cap;
   an ultrasonic transducer having a transducer head portion that generates ultrasonic vibrations;
   a container-receiving guide block for holding the container in an operating configuration in which the container's bottom end and the transducer head are in direct contact, wherein the container-receiving guide block has a top end and a bottom end and a sidewall defining a longitudinally oriented bore extending from the top end to the bottom end of the container-receiving guide block for receiving the container, wherein the bottom end aligns the closed bottom end of the container with the transducer head;
a light source for shining light into the quantity of the biological sample for measuring the turbidity of the sample;
a lid assembly, movable between an open position and a closed position, that is configured and adapted for engaging the top end of the container and urging the container toward the transducer head when the container is being held by the container-receiving guide block and the lid assembly is in the closed position, so that the container bottom surface is in contact with the transducer head and the ultrasonic vibrations generated by the transducer head is transmitted through the container wall to the sample and disperse the microbes in the sample;
wherein the lid assembly is provided with a spring-loaded mechanism formed by a hub and a receptacle nested inside the hub for engaging the top end of the container and urge the container toward the transducer head, wherein the hub is affixed to the lid assembly and having an opening through which the receptacle is received within the hub and can slide up and down, wherein the receptacle having a cavity defined by its sidewalls for receiving the top end of the container, the hub and the receptacle forming a chamber between the sidewalls of the receptacle and the hub wherein a coil spring is captured inside the chamber and urges on the receptacle downward;
a photo diode for measuring the sample's turbidity by detecting the light scattered by the microbes in the sample; and
an opening provided on the sidewall of the container-receiving guide block, the opening providing a viewing access to the container for the photo diode for measuring the sample's turbidity.

2. The apparatus of claim 1 wherein the biological sample is a liquid suspension sample.

3. The apparatus of claim 1, configured for measuring the sample's turbidity concurrently as the microbes in the sample is being dispersed.

4. The apparatus of claim 1, wherein the transducer head is provided with a recess having a chamfered edge that makes a contact with the container's bottom end for efficient transfer of ultrasonic vibration from the transducer head to the container.

5. The apparatus of claim 4, wherein the container has a cylindrical shape and the recess provided in the transducer head has a circular opening and the chamfered edge makes the contact with the container along an annular region for providing a close contact between the container bottom surface and the transducer head for efficient transfer of ultrasonic vibration from the transducer head to the container.

6. The apparatus of claim 1, wherein the light source for the turbidity measurement is provided near the top end of the container-receiving guide block.

7. The apparatus of claim 6, wherein the light source is provided with a hole for receiving the container therethrough, wherein the hole is aligned with the longitudinally oriented bore of the container-receiving guide block.

8. An apparatus for dispersing microbes in a biological sample and measuring turbidity of the biological sample, the apparatus comprising:
an ultrasonic transducer having a transducer head portion that generates ultrasonic vibrations;
a container-receiving guide block for holding a container of microbes in a biological sample in an operating configuration in which the container's bottom end and the transducer head come in direct contact, wherein the container-receiving guide block has a top end and a bottom end and a sidewall defining a longitudinally oriented bore extending from the top end to the bottom end of the container-receiving guide block for receiving the container, wherein the bottom end aligns the closed bottom end of the container with the transducer head, and wherein the container-receiving guide block provides a light source for measuring the turbidity of the biological sample;
a lid assembly, movable between an open position and a closed position, that is configured and adapted for engaging the container and urge the container toward the transducer head when the container is being held by the container-receiving guide block and the lid assembly is in the closed position, so that the container bottom surface is in direct contact with the transducer head and the ultrasonic vibrations generated by the transducer head is transmitted through the container's wall to the sample and disperse the microbes in the sample;
wherein the lid assembly is provided with a spring-loaded mechanism formed by a hub and a receptacle nested inside the hub for engaging the top end of the container and urge the container toward the transducer head, wherein the hub is affixed to the lid assembly and having an opening through which the receptacle is situated within the hub and can slide up and down, wherein the receptacle having a cavity defined by its sidewalls for receiving the top end of the container, the hub and the receptacle forming a chamber between the sidewalls of the receptacle and the hub wherein a coil spring is captured inside the chamber and urges on the receptacle downward;
a photo diode for measuring the sample's turbidity; and
an opening provided on the sidewall of the container-receiving guide block, the opening providing a viewing access to the container for the photo diode for measuring the sample's turbidity.

9. The apparatus of claim 8 wherein the biological sample is a liquid suspension sample.

10. The apparatus of claim 8, configured for measuring the liquid suspension's turbidity concurrently as the microbes in the liquid suspension is being dispersed.

11. The apparatus of claim 8, wherein the transducer head is provided with a recess having a chamfered edge that makes a contact with the container's bottom end for efficient transfer of ultrasonic vibration from the transducer head to the container.

12. The apparatus of claim 11, wherein the container has a cylindrical shape and the recess provided in the transducer head has a circular opening and the chamfered edge makes the contact with the container along an annular region for providing a close contact between the container bottom surface and the transducer head for efficient transfer of ultrasonic vibration from the transducer head to the container.

13. The apparatus of claim 8, wherein the light source for the turbidity measurement is provided near the top end of the container-receiving guide block.

14. The apparatus of claim 13, wherein the light source is provided with a hole for receiving the container therethrough, wherein the hole is aligned with the longitudinally oriented bore of the container-receiving guide block.

* * * * *